(12) United States Patent
Agnew

(10) Patent No.: US 9,415,187 B2
(45) Date of Patent: Aug. 16, 2016

(54) DIALYSIS CATHETER

(75) Inventor: Charles W. Agnew, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 498 days.

(21) Appl. No.: 13/310,014

(22) Filed: Dec. 2, 2011

(65) Prior Publication Data

US 2012/0143123 A1    Jun. 7, 2012

Related U.S. Application Data

(60) Provisional application No. 61/419,079, filed on Dec. 2, 2010.

(51) Int. Cl.
*A61M 25/00* (2006.01)
*A61M 25/04* (2006.01)
*A61M 1/36* (2006.01)

(52) U.S. Cl.
CPC ......... *A61M 25/0075* (2013.01); *A61M 1/3653* (2013.01); *A61M 1/3661* (2014.02); *A61M 25/04* (2013.01); *A61M 2025/0025* (2013.01); *A61M 2025/0031* (2013.01); *A61M 2025/0035* (2013.01); *A61M 2025/0039* (2013.01); *A61M 2025/0079* (2013.01)

(58) Field of Classification Search
CPC ............ A61M 1/0058; A61M 2025/0031; A61M 1/0084; A61M 25/0032; A61M 25/003; A61M 2001/3661; A61M 2025/0034; A61M 25/0074; A61M 1/285; A61M 2025/0073; A61M 25/0075; A61M 2039/0633; A61M 2025/1052; A61M 2039/2433; A61M 39/165; A61M 1/3621; A61M 1/3653; A61M 1/3661; A61M 2025/0025; A61M 2025/0035; A61M 2025/0039; A61M 2025/0079; A61M 25/04
USPC .................. 604/30, 33–35, 43, 104–108, 604/164.01–164.03
See application file for complete search history.

(56) References Cited

U.S. PATENT DOCUMENTS

| | | | | |
|---|---|---|---|---|
| 5,011,488 | A | * | 4/1991 | Ginsburg ............... A61B 17/22 604/104 |
| 5,423,745 | A | * | 6/1995 | Todd et al. ................... 604/500 |
| 2003/0199820 | A1 | * | 10/2003 | Constantz et al. ........ 604/101.04 |

* cited by examiner

*Primary Examiner* — Nathan R Price
*Assistant Examiner* — Weng Lee
(74) *Attorney, Agent, or Firm* — Brinks Gilson & Lione

(57) ABSTRACT

A catheter assembly used for extracorporeal treatment, such as dialysis, of blood or other body fluid, includes an outer and inner catheter in a coaxial relationship. A fluid path is provided by a passageway defined between the catheters and a distal end of the outer catheter, and another fluid path is provided through a lumen and a distal end of the inner catheter. A sealing member is coupled to one of the catheters. The member in a first position is configured to permit the distal ends of the catheters to transport fluid, while in a second position the member is configured to inhibit at least one of the distal ends from transporting fluid. The sealing member may include a flared portion for enhance sealing. The sealing member may also have a portion extending outward from the catheters to position the distal ends away from vessel contact.

14 Claims, 4 Drawing Sheets

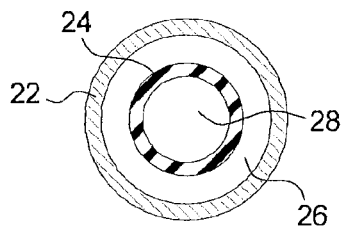
FIG. 3
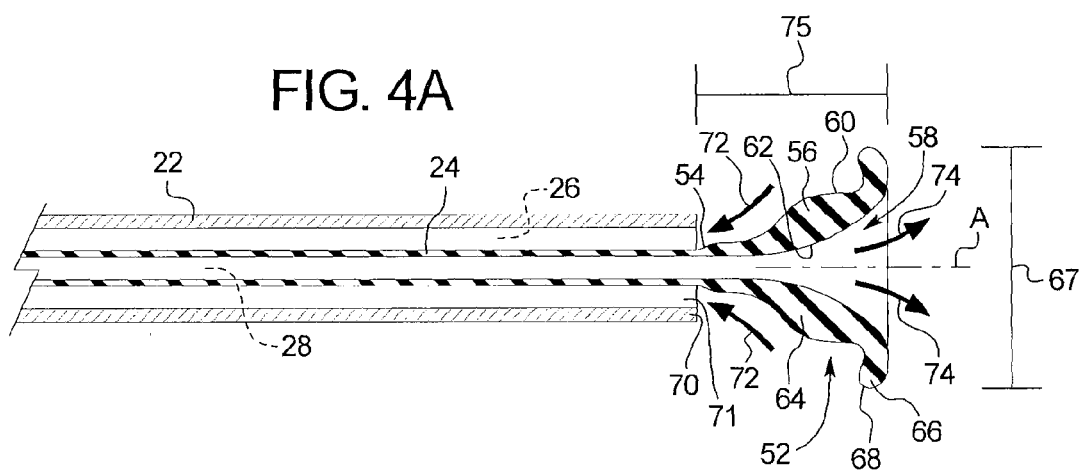
FIG. 4A
FIG. 4B
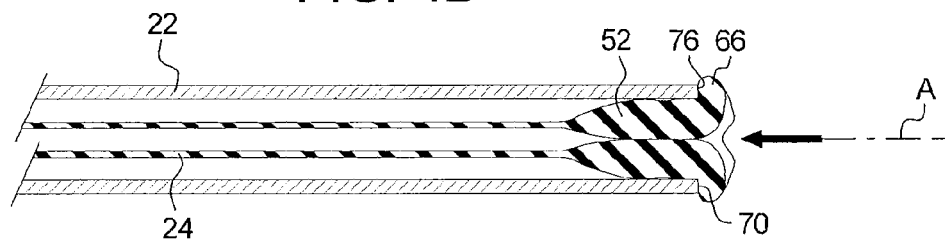
FIG. 5
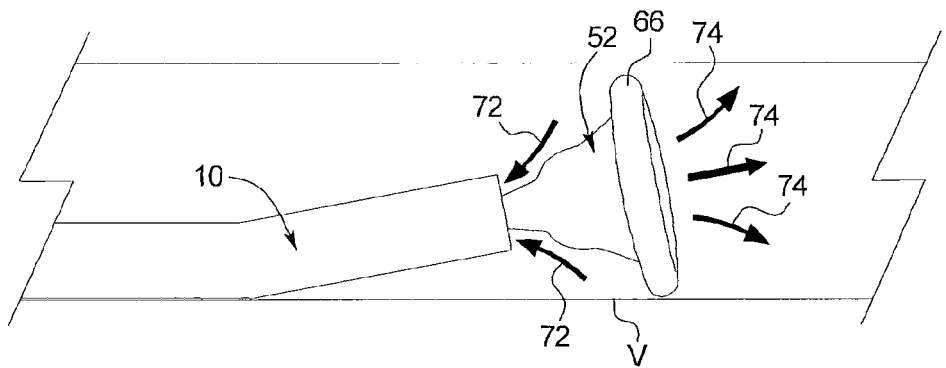

DIALYSIS CATHETER

This application claims priority to U.S. Provisional Application No. 61/419,079, filed Dec. 2, 2010, which is hereby incorporated by reference herein.

BACKGROUND

The present disclosure relates generally to a medical device for transporting fluids. More particularly, the present disclosure relates to a catheter for transporting fluids from the patient's body for extracorporeal treatment such as dialysis, and returning treated fluids to the body.

Dual lumen catheters are commonly used for transporting body fluids for treatment, such as dialysis, external of a patient's body, a process generally referred to in the medical field as "extracorporeal" treatment, and thereafter returning the treated fluid to the body. The fluid is withdrawn from the body through one of the lumens of the catheter, generally referred to as the withdrawal or aspiration lumen. The fluid is subjected to a treatment process, and thereafter returned to the body through the other lumen, generally referred to as the infusion or return lumen.

In many cases, the extracorporeal treatment is carried out as part of a hemodialysis procedure. During hemodialysis, blood is withdrawn from a blood vessel through the aspiration lumen and routed to a dialyzer for cleansing. The cleansed blood is then returned to the vessel through the infusion lumen. When such a catheter is used for hemodialysis, whether for short-term hemodialysis (generally thirty days or less) or longer-term hemodialysis (generally greater than thirty days), it is generally inserted into the body through the internal jugular vein, subclavian vein or femoral vein. In addition to hemodialysis, extracorporeal catheters can also be used for other procedures, such as pheresis and hemofiltration, in which a fluid is removed from the body for treatment and later returned to the body.

Among the types of commercially available dual lumen catheters used for dialysis are dual D-shaped lumen catheters and coaxial catheters. In some instances, dual D-shaped lumen catheters may be more undesirable. For example, for a given pressure, the rate of fluid flow through a D-shaped lumen catheter is typically less than the flow rate for a circular cross-sectioned lumen in a coaxial catheter of comparable area. One reason for this pressure disadvantage is that there is generally more turbulence and backpressure generated through a D-shaped lumen catheter. Moreover, internal crevices of a D-shaped lumen catheter can increase the risk of blood clot formation.

Recirculation of treated fluid is another factor to consider for dialysis catheters. Recirculation is problematic when a majority of untreated blood that is aspirated through the aspiration lumen is the same fluid that was just previously treated and returned to the body vessel. As a result, the overall duration of treatment is lengthened, thereby inconveniencing the patient.

In regard to dialysis coaxial catheters, some coaxial catheters for use in dialysis can have a freely dangling inner catheter at the distal end of the outer catheter. Consequently, vacuum used to withdraw fluid may tend to pull the inner catheter toward the interior wall of the outer catheter, thereby undesirably occluding inflow side ports that are formed in the outer catheter wall. Once flow is partially occluded in a manner to sufficiently affect the inflow hemodynamics, the dialysis treatment suffers and the treatment is lengthened. Furthermore, the formation of fibrin sheaths along the inflow side ports can also cause undesirable occlusion. Fibrin sheaths are formed, e.g., in response to the vessel wall washing effect or clotting.

Thus, what is needed is an improved catheter configuration for use in extracorporeal treatment of body fluids such as dialysis. In particular, what is needed is a catheter configuration that is structured and arranged in a manner to inhibit recirculation of treated fluid for retreatment. Further, the catheter configuration is structured and arranged in a manner to ensure that inflow and outflow ports are not restricted in any appreciable way so that extracorporeal fluid treatment is more effective.

SUMMARY

In one embodiment, a catheter assembly including an outer tubular member and an inner tubular member is provided for extracorporeal treatment, such as dialysis, of blood or other body fluid. The outer tubular member can have a passageway extending therethrough and a distal end opening. The inner tubular member can have a lumen extending therethrough and a distal end opening, which together define a first passage of fluid in a first direction. The inner catheter can be situated within the passageway of the outer catheter to define an annular lumen therebetween. The annular lumen and the distal end opening of the outer tubular member can define a second passage of fluid in a second direction, opposite the first direction. The catheter assembly can include a collapsible sealing structure axially movable between a first position and a second position. In the first position, the sealing structure is configured to protect and facilitate fluid flow through the distal end openings of the respective inner and outer tubular members. In the second position, the sealing structure is collapsed to form a seal at both of the distal end openings of the respective inner and outer tubular members to inhibit fluid flow therethrough.

In other aspects, the sealing structure may include a flared portion configured to sealably engage one of the distal end opening of the inner tubular member and the distal end opening of the outer tubular member. The sealing structure may include an enlarged portion configured to position at least one of the distal end opening the inner tubular member and the distal end opening of the outer tubular member away from vessel contact. The sealing structure may be coupled to either the inner tubular member or the outer tubular member.

In another embodiment of a catheter assembly, an outer tubular member and an inner tubular member that is situated within the outer tubular member define an annular lumen therebetween. The inner tubular member can have a lumen extending therethrough and a distal end opening, which together can define a first fluid passage. The inner tubular member can be connectable to an extracorporeal treatment unit in order to infuse or aspirate fluid in a first direction through the first fluid passage. The annular lumen together with a distal end opening of the outer tubular member can define a second fluid passage. The outer tubular member can be connectable to the extracorporeal treatment unit in order to infuse or aspirate fluid in a second direction, opposite the first direction, through the second fluid passage. A collapsible distal tip is coupled to one of the inner and outer tubular members. In a first position, a portion of the distal tip can be radially extended beyond the tubular members to protect and facilitate fluid flow through the distal end openings of the respective inner and outer tubular members. In a second position, a portion of the distal tip can be at least partially collapsed to form a seal at both of the distal end openings of the respective inner and outer tubular members to inhibit fluid flow therethrough.

In accordance with yet another embodiment, a method for treating body fluid of a body vessel with an extracorporeal treatment unit is provided. The method can include one or more of the following steps: translating an end of a catheter assembly with a sealing structure at the end thereof in a first position to a treatment site of said body vessel; axially moving the sealing structure from the first position to a second position; aspirating body fluid to be treated from the body vessel through one of the distal end openings of the respective inner and outer tubular members, and transporting the aspirated body fluid to an extracorporeal treatment unit for treating the body fluid; and transporting the treated fluid from the extracorporeal treatment unit, and infusing the treated fluid into the body vessel through the other of the distal end openings of the respective inner and outer tubular members. The catheter assembly can also be configured so that the flushing of the annular lumen and the lumen of the inner catheter with a flushing fluid can occur simultaneously when the sealing structure is in the first position.

BRIEF DESCRIPTION OF THE DRAWINGS

FIG. 3 is a longitudinal sectional view of the catheter assembly taken along line 3-3 of FIG. 1.

FIG. 4A is a longitudinal sectional view of a distal end of the catheter assembly in an extended position.

FIG. 4B is a longitudinal sectional view of a distal end of the catheter assembly in a retracted position.

FIG. 5 is a side view depicting a distal portion of the catheter assembly within a body vessel.

DETAILED DESCRIPTION OF THE DRAWINGS AND THE PRESENTLY PREFERRED EMBODIMENTS

Figure 1:
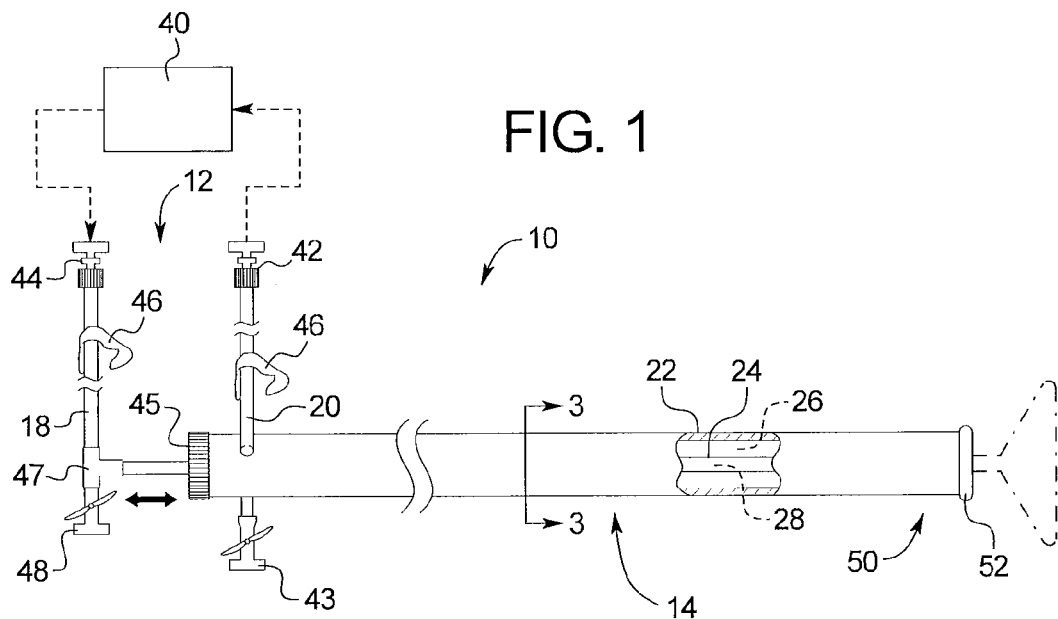
FIG. 1 is a side view, partially sectioned, of a catheter assembly coupled to an extracorporeal treatment unit.

For purposes of promoting an understanding of the present disclosure, reference will now be made to the embodiments illustrated in the drawings, and specific language will be used to describe the same. The following detailed description of the preferred embodiments will make clear the preferred arrangement, size relationships and manner of using the components shown herein.

In the following discussion, the terms "proximal" and "distal" will be used to describe the axial ends of the catheter, as well as the axial ends of various component features. The "proximal" end is used in conventional manner to refer to the end of the catheter (or component) that is closest to the operator during use of the assembly. The "distal" end is used in conventional manner to refer to the end of the catheter (or component) that is initially inserted into the patient, or that is closest to the patient.

Those skilled in the art will appreciate that the catheter assembly described herein is suitable for multiple uses involving inflow and outflow of body fluids from a body vessel of a patient. However, hereinafter the present disclosure will be primarily described with reference to one of its intended uses, namely as a hemodialysis catheter for use in the extracorporeal treatment of blood. Preferably, the hemodialysis catheter can enable blood inflow without disturbance, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such additional procedures. The dimensions and configurations of various components described herein are particular suitable for use in extracorporeal treatment, although the dimensions can vary as needed depending on the type of use in other applications.

Various embodiments of the catheter assembly described herein are structured and arranged in a manner to decrease the risk of recirculation of treated fluid and to decrease the risk of occlusion of the aspiration openings from vessel contact. This arrangement can enhance the efficiency of the extracorporeal procedure by assuring that the majority of untreated blood that is aspirated through the desired access opening is not the same blood previously treated and returned to the body vessel through the other access opening. Accordingly, the overall duration of treatment is desirably shortened for the convenience of the patient and operator.

FIG. 1 depicts a catheter assembly 10 having a proximal portion 12 and a catheter body 14 that extends distally from proximal portion 12. A pair of extension tubes 18, 20, can extend away from proximal portion 12. Extension tubes 18, 20 can comprise generally of flexible polymers commonly used for such purposes in the medical device art, such as polyurethane, polyvinylchloride (PVC), and silicone.

Catheter body 14 can include an outer catheter 22 and an inner catheter 24, each of which are generally tubular members having a lumen extending therethrough. Preferably, outer catheter 22 and inner catheter 24 are in a coaxial relationship, thereby forming an annular lumen between an interior wall portion of outer catheter 22 and an outer wall portion of inner catheter 24, as shown in FIG. 3. To this end, the outer wall portion of the outer catheter generally defines the outer wall of the catheter body. The respective lumens of outer catheter 22 and inner catheter 24 can extend along the entire length of their respective bodies, and can correspond to the number of extension tubes. It can be appreciated by one skilled in the art that either the annular lumen or the inner catheter lumen can be used for infusion or aspiration of blood; however, preferably the annular lumen is used for blood aspiration and the inner catheter lumen is used for blood infusion. Thus, hereinafter the annular lumen will be referred to as an aspiration lumen 26 and the inner catheter lumen will be referred to as an infusion lumen 28.

Accordingly, extension tube 20 communicates with aspiration lumen 26 for receiving blood withdrawn from the body vessel in the patient and transporting blood to an extracorporeal treatment unit 40, such as a dialyzer. A luer lock or other suitable connector 42 is fitted onto the proximal end of extension tube 20 in conventional fashion. During use of catheter assembly 10, connector 42 is engaged in mating relationship with a connector associated with an ingress opening of extracorporeal treatment unit 40 for establishing a flow path of blood to the extracorporeal treatment unit. Extension tube 20 can be coupled to outer catheter 22 through a side port formed in the wall thereof. Another portion of the outer catheter may have another side port with a valve coupling 43 fitted therein. As can be appreciated by those skilled in the art, valve coupling 43 has a connector end for coupling to a fluid source, such as for flushing, and a valve member that can be opened or closed for regulating fluid flow therethrough. Connectors can be fitted within any of the side ports to enhance attachment of the respective devices to the outer catheter.

Furthermore, extension tube 18 communicates with infusion lumen 28. A luer lock or other suitable connector 44 is fitted onto the proximal end of extension tube 18. During use, connector 44 is engaged in mating relationship with a connector associated with an egress opening of extracorporeal treatment unit 40 for receiving treated blood from the extracorporeal treatment unit, where the treated blood is returned to infusion lumen 28 for reentry into the body. Extracorporeal treatment unit 40 and its ingress and egress openings are shown schematically in FIG. 1. Conventional clamps 46 may be provided along the exterior of the extensions tubes for selectively closing off the blood flow between the extracorporeal treatment unit and the catheter body when not the extracorporeal treatment unit is not in use.

Inner catheter 24 is shown extending beyond the proximal end of outer catheter 22. Extension tube 20 can be coupled to inner catheter 24, directly or indirectly, through a T-fitting connector 47. The inner catheter is shown extending beyond the proximal end of the outer catheter. To this end, a seal 45 is provided between the outer catheter and the inner catheter. Seal 45 is configured to prevent leakage of fluid from the annular lumen through the axial proximal opening from which the inner catheter extends, and permit rotation and axial translation of the inner catheter relative to the outer catheter. Connector 47 can have a first end attached to a proximal end of the inner catheter or an extension thereof; a second end attached to the distal end of extension tube 20; and a third end coupled to a valve coupling 48. As can be appreciated by those skilled in the art, valve coupling 48 has a connector end for coupling to a fluid source, such as for flushing, and a valve member that can be opened or closed for regulating fluid flow therethrough.

A guard and sealing structure can be provided with the catheter assembly. The guard and sealing structure can be positioned, such as extended axially outward from the catheter assembly, to protect and maintain the patency of the access openings leading to the respective aspiration lumen and infusion lumen. The guard and sealing structure can also be positioned, such as collapsed within the lumen of the outer catheter, in order to form a seal at least at one of the access openings leading to the respective aspiration lumen and infusion lumen to inhibit or substantially block fluid flow therethrough.

Figure 2:
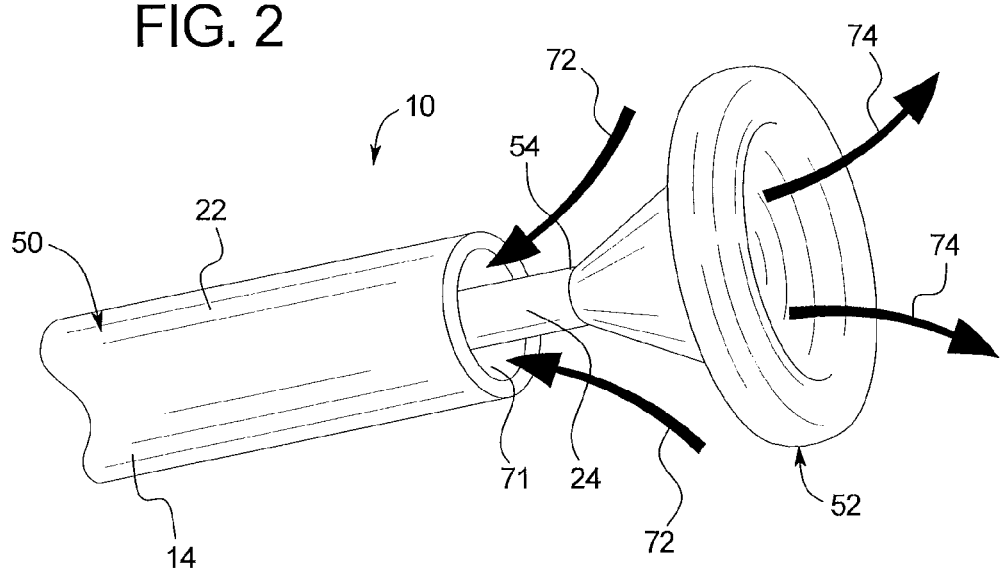
FIG. 2 is an enlarged perspective view of a distal end of the catheter assembly of FIG. 1, depicting a distal tip in an open configuration.

FIG. 2 depicts one embodiment of the guard and sealing structure comprising an enlarged distal tip 52 coupled to the distal end 54 of inner catheter 24. The outermost cross-sectional area of distal tip 52 is configured to inhibit recirculation of treated blood from the infusion lumen and into aspiration lumen 26. For instance, the outermost cross-sectional area of the distal tip can be at least greater than the cross-sectional area of the outer catheter. With additional reference to FIG. 4A, distal tip 52 includes a wall 56 having an outer surface 60 and an inner surface 62. Wall 56 is spaced from an axis A of the catheter body to define an infusion opening 58 that is in communication with infusion lumen 28. In one example, wall 56 is generally spaced radially from an axis A at an increasingly larger distance in the distal direction to define a flared distal tip. Outer surface 60 and inner surface 62 may be substantially parallel such that the wall has a constant thickness or obliquely oriented to one another to define a wall with a varied thickness.

Outer surface 60 of the distal tip may further include a protruding region 64 to facilitate closure of the distal tip as will be described below. Inner surface 62 of the distal tip can be curved outward to facilitate a more laminar outflow such that the blood can flow farther distally away from the distal end of the distal tip to minimize recirculation. Infusion opening 58 can be spaced radially from axis A at an increasingly larger distance in the distal direction, such as shown in FIG. 4A, to provide a smoother transition for the blood exiting infusion lumen 28 and entering into the body vessel. However, as appreciated by those skilled in the art, the infusion opening may have a constant diameter throughout the body of the distal tip.

An outer lip 66 may be formed at the distal end of distal tip 52. Outer lip 66 can extend radially outward to define the maximum radial extent of the distal tip, shown as distance 67, at the distal end thereof, although the distal tip can have the radial distance 67 without the outer lip feature. Outer lip 66 may be further sized to sealably contact the vessel wall to further inhibit recirculation of treated blood into the aspiration lumen. To facilitate this sealing action, a curved outer surface 68 may be provided along outer lip 66. The combination of a flared wall of the distal tip and the outer lip as shown in the figures can define a distal tip having a trumpet shape.

Distal tip 52 can be axially movable between an extended position and a retracted position. The extended position is shown in FIGS. 2 and 4A, where the distal tip has an open configuration. The retracted position is shown in FIG. 4B, where the distal tip is moved to a collapsed configuration. Axial movement of distal tip 52 can be achieved by relative movement between inner catheter 24 and outer catheter 22, which can be controlled by an operator at the proximal portion of the catheter assembly.

In the extended position, distal tip 52 is located distally beyond a distal end 70 of outer catheter 22. In particular, distal tip 52 can be moved away from distal end 70 so that the distal tip can assume the open configuration. In this position, an inflow fluid path is formed, represented by arrows 72, from an aspiration opening 71 that is through distal end 70 of outer catheter 22 and to aspiration lumen 26. Also formed is an outflow fluid path, represented by arrows 74, from infusion lumen 28 and infusion opening 58 of distal tip 52. The distance 75 of extension of distal tip 52 from distal end 70 of outer catheter 22 can be any distance sufficient to inhibit recirculation. It can be appreciated that a longer extension distance will further reduce the risk of recirculation. It can also be appreciated that a greater cross-sectional area of the distal tip as defined by the radial distance 67 can also provide a larger barrier to recirculation.

FIG. 5 is representative of how the guard and sealing structure can position the aspiration ports away from the vessel wall. For example, distal tip 52 and catheters 22, 24 can be structured and arranged to facilitate the placement of aspiration opening 71 away from contacting the body vessel wall V, which is shown in FIG. 5. For instance, the extension distance 75, the radial distance 67, the flaring rate of the distal tip, or any combination thereof can suspend the distal end of the outer catheter away from contacting the body vessel wall. As a result, the risk of occlusion of the aspiration opening and the aspiration lumen can be reduced. Having a primary aspiration opening through distal end 70 of outer catheter 22 can minimize occlusive effects of side port blockage when positioned against the vessel wall. It can be appreciated though by those skilled in the art that any number of aspiration side ports (e.g., 0.07 inches in diameter) may be formed in the wall of the outer catheter, in addition to the aspiration opening at the axial end of the catheter, to facilitate fluid aspiration.

In the retracted position, a substantial portion of distal tip 52 can be situated within a portion of the lumen of outer catheter 22 proximate distal end 70 to define the collapsed configuration. In the collapsed configuration, distal tip 52 is configured to inhibit blood outflow through infusion opening 58, and may be further configured to inhibit blood inflow through aspiration opening 71, or both, as well as blood flow through their respective lumens. Preferably, when distal tip 52 is in the collapsed configuration and the retracted position, a seal can be formed that is suitable to inhibit the fluid flow path through both of the aspiration and infusion lumens, as described below. This feature can be beneficial as the operator can simultaneously flush both lumens, thereby expediting the overall procedure.

Distal tip 52 can be made of a flexible biocompatible material. The material may also be resilient, with the distal tip having a bias in the open configuration, as shown in FIG. 2. To facilitate collapsibility and sealing, the distal tip member can be made of a low durometer material such as but not limited to elastomers, rubbers, polyurethanes, and silicones. The material of the distal tip can be configured to permit the distal tip to collapse and conform to the shape of the lumen of the outer catheter in order to fill the lumen when retracting the distal tip within the outer catheter.

The flexibility of the distal tip can facilitate closure thereof when moving from the open configuration and the extended position to the collapsed configuration and the retracted position. For example, as distal tip 52 is retracted into the lumen of outer catheter 22, the edge 76 of distal end 70 of outer catheter 22 can slide along outer surface 60 of the distal tip. Wall 56 of distal tip 52 can then be displaced radially inward toward axis A. As shown in FIG. 4B, outer lip 66 may also define a physical block to prevent farther axial movement of distal tip 52 within outer catheter 22. When engaged with edge 76, outer lip 66 can also provide a sealing surface along the entire edge 76 of the outer catheter to further inhibit blood flow through the aspiration opening.

Also, with reference to FIG. 4B, the thickness of wall 56 of the distal tip is selected preferably to fill the cross-sectional area of at least the lumen of outer catheter 22. The thickness of wall 56 of the distal tip is generally greater than the wall thickness of the inner catheter. When present, protruding region 64 of distal tip 52 can enhance closure of the distal tip. For example, when the edge 76 engages protruding region 64, wall 56 of distal tip 52 is urged to fold radially inward toward axis A to enhance collapsibility thereof.

Figure 6:
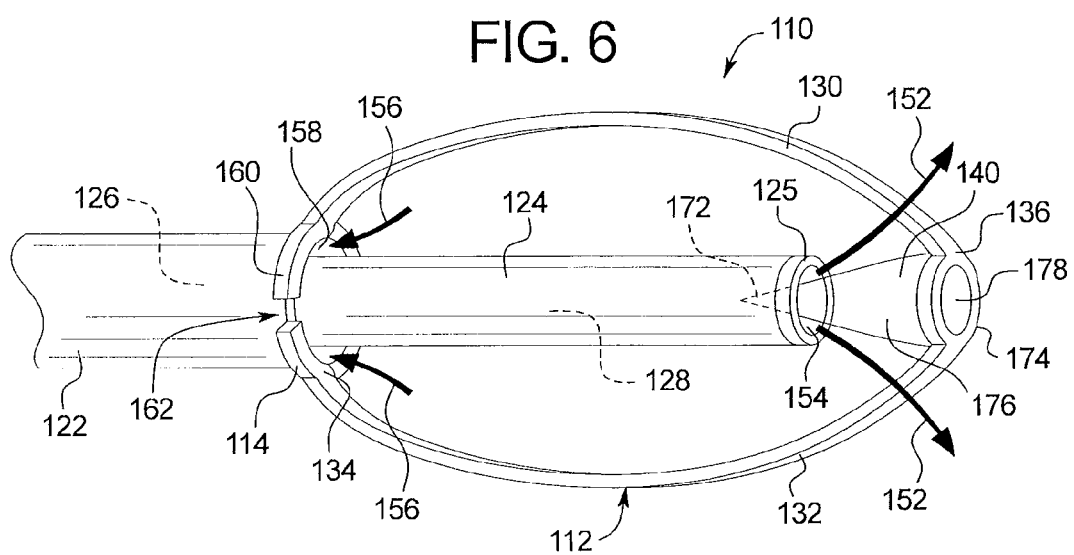
FIG. 6 is a side view of a distal end of another embodiment of a catheter assembly, depicting a distal tip in an open configuration.

FIG. 6 depicts a distal portion of a catheter assembly 110 with another embodiment of the guard and sealing structure that comprises an enlarged distal tip 112 coupled to the distal end 114 of the outer catheter 122. The catheter assembly 110 can include any of the features described with respect to the catheter assembly 10, except what is described in the following.

Distal tip 112 can include one or more arms (shown as a first arm 130 and a second arm 132) and an axial protruding member 140. The arms 130, 132 can have a proximal end 134 coupled to outer catheter 122 and a distal end 136 coupled to axial protruding member 140. A sealing member 160 can be attached to the arms 130, 132. Sealing member 160 may be configured to form a seal along the inner catheter 124.

Figure 7:
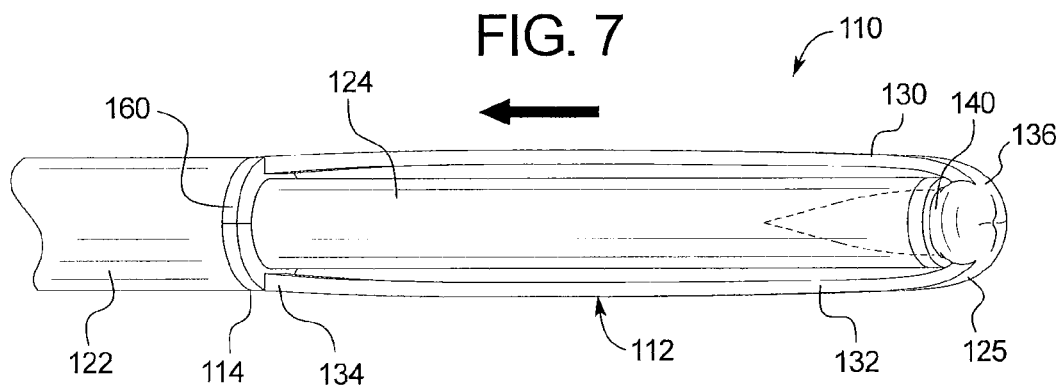
FIG. 7 is a side view of a distal end of the catheter assembly in FIG. 6, depicting a distal tip in a collapsed configuration.

Distal tip 112 can be axially movable between an extended position, as shown in FIG. 6, whereby the distal tip has an open configuration; and a retracted position shown in FIG. 7, whereby the distal tip is moved to a collapsed configuration. Movement of distal tip 112 can be achieved by relative movement between inner catheter 124 and outer catheter 122, which can be controlled by an operator at the proximal portion of the catheter assembly.

In the extended position, a portion of distal tip 112, such as axially protruding member 140, is located distally beyond the distal end 125 of inner catheter 124. In this position, the outflow fluid path, represented by arrows 152, from the infusion lumen 128 and the infusion opening 154 formed through the distal end 125 of inner catheter 124. Also formed is the inflow fluid path is formed, represented by arrows 156, from the aspiration opening 158. Aspiration opening 158 can be formed through distal end 114 of outer catheter 122 to lead to the aspiration lumen 126 formed between the inner catheter and the outer catheter.

In FIG. 6, arms 130, 132 can flex outward away from the axis by a distance that can be generally greater than or beyond the outer catheter when distal tip 112 is in the extended position. This arrangement can facilitate the positioning of at least one of distal ends 114, 125 of the respective outer and inner catheters away from contacting the vessel wall. Arms 130, 132 can be flexed outwardly by relative movement between the distal end 114 of outer catheter 122 and the distal end 125 of inner catheter 124 toward one another, thereby allowing the distal tip to assume the open configuration. To this end, axially protruding member 140 is positioned away from the infusion opening 154 so that the outflow path is formed. Although the arms can assume a bowed configuration so that the arms are curved inwardly, the arms can be formed in any configuration to accomplish the same outcome. The arms are shown as elongated members that are axially oriented. However, it is contemplated that the arms can be formed into additional shapes such as sinusoidal, zigzag, helical, or the like, which can be particular useful when only one arm is used. Additional interconnecting members may be used to attach intermediate portions of the arm to provide additional support.

In FIG. 7, arms 130, 132 can flex inward toward the axis proximately along inner catheter 124 to form a smaller profile than in the extended position, when distal tip 112 is in the retracted position. Arms 130, 132 can be flexed inwardly by relative movement between the distal end 114 of outer catheter 122 and the distal end 125 of inner catheter 124 away from one another, thereby allowing the distal tip to assume the closed configuration. To this end, axially protruding member 140 can be positioned in sealable contact with the infusion opening 154 so that the outflow path is substantially blocked. It is contemplated that the arms may be biased in either the open configuration (FIG. 6) or the closed position (FIG. 7).

Sealing member 160 is configured to allow inflow of fluid through aspiration opening 158 when the distal tip is in the extended position, as shown in FIG. 6, and to inhibit fluid flow through aspiration opening 158 when the distal tip is in the retracted position, as shown in FIG. 7.

Sealing member 160 can comprise a ring or similar structure that at least partially surrounds inner catheter 124. In other words, the sealing structure may completely surround the inner catheter without any gaps, or may include at least one circumferential gap 162 in the structure, as shown in FIG. 6. Gap 162 can permit the arms to radially expand the sealing member 160 away from contact with inner catheter 124. Sealing member 160 can be attached to the inner face of arms 130, 132, although the sealing member can be formed integrally with the arms. Optionally, the sealing member can be attached to the distal end of the outer catheter or formed integrally with the outer catheter.

Figure 8A:
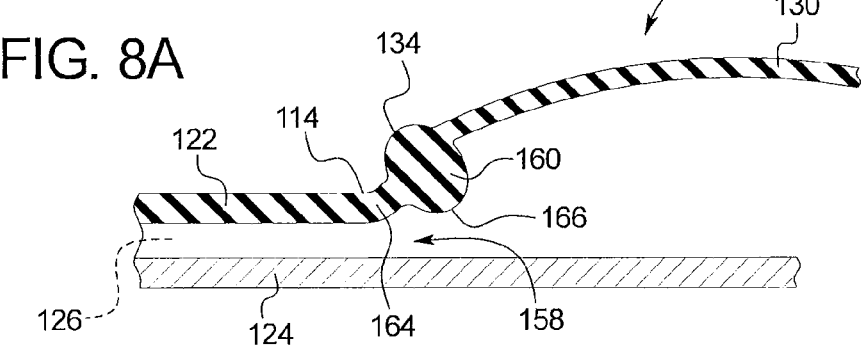
FIG. 8A is a partial sectional view of the catheter assembly in FIG. 6, depicting a sealing member positioned away from an inner catheter.
Figure 8B:
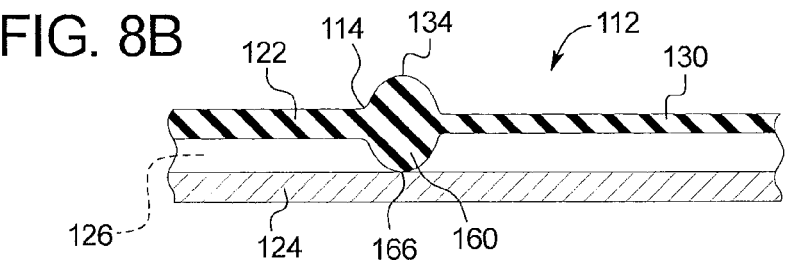
FIG. 8B is a partial sectional view of the catheter assembly in FIG. 7, depicting a sealing member positioned against an inner catheter.

FIG. 8A depicts the arm 130 coupled to the distal end 114 of outer catheter 122 in a manner to form a hinge 164, so that the arm 130 can flex outward and inward with movement of distal tip 112. Here, distal tip 112 is in the extended position and arm 130 is flexed outward. Consequently, sealing surface 166 of sealing member 160 can be moved radially away from sealable contact with the inner catheter 124, thereby forming the inflow path through aspiration opening 158. To facilitate sealability, the sealing surface can be rounded. In FIG. 8B, distal tip 112 is in the retracted position and arm 130 can be flexed inward. Here, sealing surface 166 of sealing member 160 can be moved radially to sealable contact with inner catheter 124 to substantially block the inflow path. Further, as shown in FIG. 7, gap 162 when present can be closed so that the respective ends of the sealing member components can be in sealable contact with one another.

According to FIG. 7, a substantial portion of axially protruding member 140 can be situated within a portion of the lumen of inner catheter 124 proximate distal end 125 to define a collapsed configuration of protruding member 140. Axially protruding member 140 may have a conical shape including a proximal tip 172, a distal base 174, and a flared portion 176 therebetween, as shown in FIG. 6. Distal base 174 can be coupled to distal ends 136 of arms 130, 132 so that the proximal tip 172 can be positionable within distal end 125 of inner catheter 124. Axially protruding member 140 can also be hollowed with a cavity 178 extending therethrough to facilitate radial collapsibility of axially protruding member 140 when distal tip 112 is being moved to the retracted position. In the collapsed configuration, axially protruding member 140 is configured to inhibit blood outflow through infusion opening 158. The axially protruding member can be formed into other shapes such a spherical, pyramidical, etc. so long as it can sealably engage infusion opening 154.

The aspiration and infusion lumens and the aspiration and infusion openings are preferably sized to balance infusion and aspiration blood flow rates, while maximizing the ratio of lumen space to catheter body material. For instance, where catheters experience decreased blood flow rates over time due to occlusion of the aspiration and/or infusion openings, the aspiration lumen can be sized to permit sufficient blood flow rate for continuous extracorporeal treatment without stoppage for such case. The desired flow rate within the catheters will be dependent on the ratings of the dialyzer, which is typically 300 mL/mm, but can be up to 500 mL/mm when the respective catheters and lumens are suitably sized.

The inner and outer catheters can be formed of a conventional polymer commonly used for such purposes in medical catheters, such as radiopaque polyurethane. Other conventional materials used for such purposes in the medical device art may be substituted. Non-limiting examples of such materials include polyether block amide, polyamide (nylon), silicone, polyurethane, and polytetrafluoroethylene (PTFE). Both catheters may comprise a multiple layered wall construction, with one of the layers being a reinforcement structural layer such as a coil and/or a braid to improve resistance to kinking, pushability, tractability, etc. For instance, to increase the column strength and pushability, the inner catheter may be constructed of FLEXOR® tubing construction, available from Cook, Inc (Bloomington, Ind.). Assembling of a multiple layered catheter wall is described in, e.g., U.S. Pat. No. 5,380,304 to Parker and U.S. Pat. No. 6,704,122 to Parker et al., each of which is incorporated herein by reference in its entirety.

The features described above can be supplemented with other known materials and techniques to improve various properties of the catheter assembly. For example, one or more radiopaque markers can be added along the length of the catheters, or a radiopaque material may be added to the matrix of all or a part of the catheters to improve visualization of the catheters in accordance with well-known techniques. Similarly, the catheters, and in particular the outer catheter, may include a hydrophilic coating along all or a part of the length of the catheter to facilitate entry into the vessel. As yet another alternative, the catheters can be coated or impregnated with various medicaments along all or a part of the length of the catheter body. Non-limiting examples of such medicaments include antiproliferatives, anticoagulants, thrombolytics, fibrinolytics, and antimicrobials.

Figure 9:
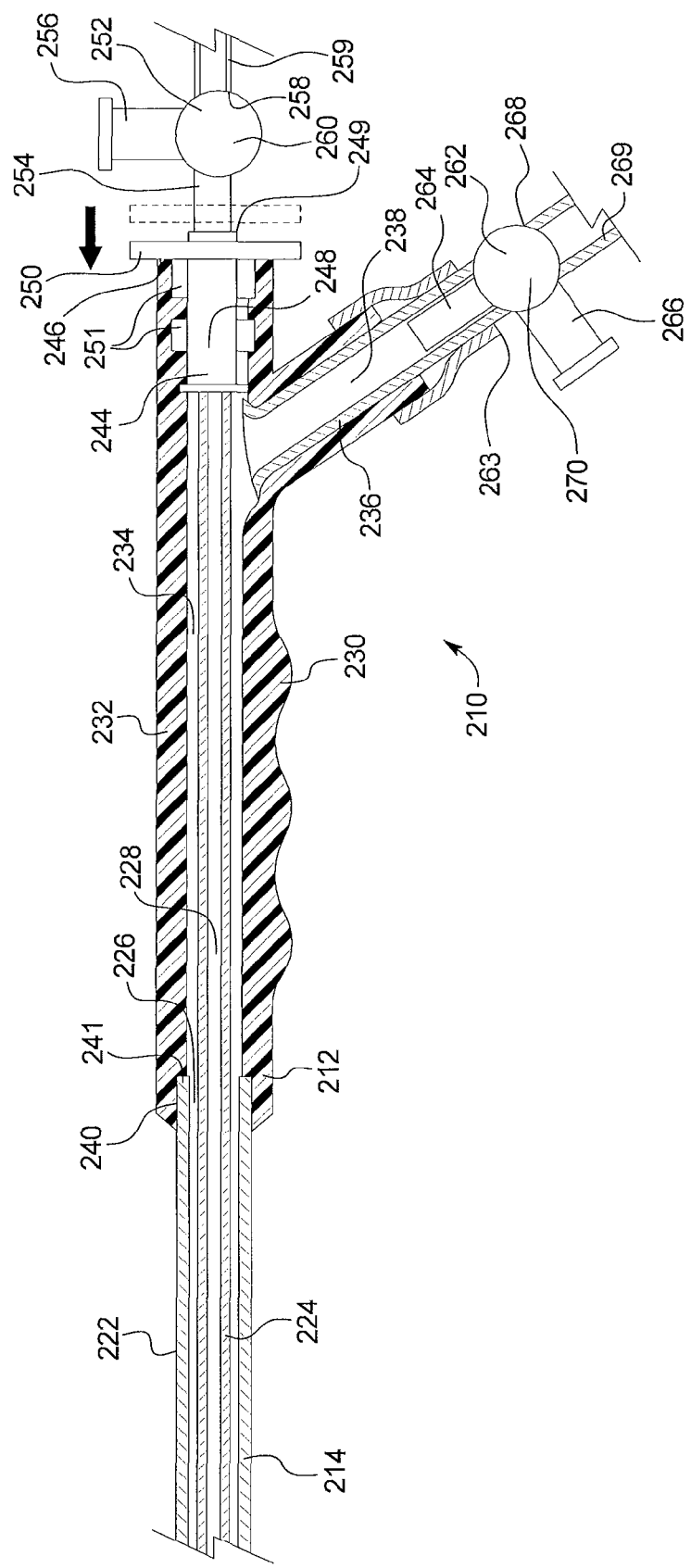
FIG. 9 is a cross-sectional view of a proximal handle of a catheter assembly.

FIG. 9 depicts a proximal portion 212 of another example of a catheter assembly 210 for use with the guard and sealing structures provided herein. Catheter assembly 210 can include a catheter body 214 extending distally from proximal portion 212. Catheter body 214 can include an outer catheter 222 and an inner catheter 224 in a coaxial relationship. The annular lumen will be referred to as an aspiration lumen 226 for the aspiration of blood and the inner catheter lumen will be referred to as an infusion lumen 228 for the infusion of blood during dialysis, although the lumens can be used for the other application.

The proximal portion 212 can be in the form of a handle 230 having a primary tubular portion 232 with a first bore 234 extending therethrough and a branch tubular portion 236 with a second bore 238 extending therethrough in communication with first bore 234. Handle 230 can be molded from a rigid plastic, and may further include contouring configured to be received in a hand such as finger grips. Handle 230 can include a recessed distal opening 240 for receiving a proximal end 241 of outer catheter 222. Proximal end 241 can be fixed within recessed distal opening 240 by any means known in the art such as an adhesive or by insert molding.

Inner catheter 224 can extend through tubular portion 232. A proximal end 243 of inner catheter 224 can be coupled to a movable sleeve 244. Movable sleeve 244 can extend through tubular portion 232 and extend beyond a proximal end 246 of handle 230. Movable sleeve 244 can include an aperture 248 extending therethrough that is communication with infusion lumen 228. Movable sleeve 244 can further include a ring 250 at its proximal end 249. Ring 250 is generally larger in cross-sectional area that the primary tubular portion 232, and can be used as the primary means for moving the inner catheter relative to the outer catheter. One or more sealing members 251, such as O-rings, can be applied around movable sleeve 244 and in between the inner wall of the primary tubular portion 232. Sealing member 251 can be configured to inhibit leakage of fluid within the first bore out of the proximal end of the handle, while permitting movement of movable sleeve.

A first valve member 252, such as a stop cock, can be coupled to proximal end 249 of movable sleeve 244. First valve coupling 252 can have a first leg 254 coupled to the movable sleeve 244, a second leg 256 with a connector end for coupling to a fluid source, such as for flushing, and a connector end 258 for coupling to an extension tube 259. Extension tube 259 is coupled to the extracorporeal treatment unit. A valve member 260 can be configured to be opened or closed for regulating fluid flow therethrough and directing fluid from second leg 256 or from connector end 258 to first leg 254. A second valve member 262, such as a stop cock, can be coupled to a proximal end 263 of branch tubular portion 236. Second valve coupling 262 has a first leg 264 coupled to branch tubular portion 236, a second leg 266 with a connector end for coupling to a fluid source, such as for flushing, and a connector end 268 for coupling to an extension tube 269. Extension tube 269 is coupled to the extracorporeal treatment unit. A valve member 270 can be configured to be opened or closed for regulating fluid flow therethrough and directing fluid from second leg 266 or from first leg 264 to connector end 268. Accordingly, extension tube 269 communicates with aspiration lumen 226 for receiving blood withdrawn from the body vessel in the patient and transporting blood to an extracorporeal treatment unit, such as a dialyzer. Furthermore, extension tube 259 communicates with infusion lumen 228 for returning treated blood for reentry into the body.

The distal tip can be axially movable between an extended position and a retracted position as described above. Axial movement of the distal tip can be achieved by relative movement between inner catheter 224 and outer catheter 222, which can be controlled by an operator at the proximal portion of the catheter assembly. This relative movement can be achieved by movable sleeve 244. Movable sleeve 244 can be moved between an open position and a closed position. In the open position, ring 250 of movable sleeve 244 is placed against proximal end 246 of handle 230 (shown presently in FIG. 9) to cause the distal tip to move to the extended position. In the closed position, ring 250 of movable sleeve 244 is moved away from proximal end 246 of handle 230 to a proximal position (shown in dashed lines in FIG. 9), to cause the distal tip to move to the retracted position. In one example, movable sleeve 244 and valve member 252 are coupled in a fixed relationship so that movement of both causes movement of the inner catheter. In another example, movable sleeve 244 and valve member 252 are coupled in a manner where the movable sleeve can slide over the first leg 254 with the valve member 252 is a fixed position in order to cause movement of the inner catheter.

In preparation for operation of the catheter assembly, the operator can flush the aspiration and infusion lumens with a flushing fluid, such as saline or herapinized saline, before insertion into the body and/or after translation to the treatment site. To flush the catheter assembly, the guard and sealing structure can be moved to the retracted position and the collapsed position, as shown in FIGS. 4B and 7. As described above, a seal may be formed at the respective distal end openings to close the aspiration opening and the infusion open so that the operator can simultaneously flush both lumens from the proximal end. A flushing fluid source can be coupled to the connector end of the valve coupling of the outer catheter and/or the valve coupling of the inner catheter. The valve member can then be opened to allow flushing fluid under pressure to transport the fluid to the respective lumens. The clamps on the extension tubes may need to be clamped to the closed position in order to urge the flushing fluid toward aspiration and infusion lumens. After satisfactory flushing, the valve member can be then closed.

Insertion of the catheter assembly into the body vessel may be accomplished by any technique known in the art. For example, a distal portion of the catheter assembly can be inserted into the body vessel over a wire guide, such as via the well-known Seldinger percutaneous entry technique. The connectors of the respective extension tubes can be engaged in mating relationship with a connector associated with the respective ingress and egress openings of the extracorporeal treatment unit. The distal portion of the catheter body can be inserted into the vessel with the guard and sealing structure in the retracted position, and then translated to a site for removal of fluid for treatment.

To operate the catheter assembly with the extracorporeal treatment unit, the guard and sealing structure can be moved to the extended position with relative movement between the inner catheter and the outer catheter. For example, with reference to FIG. 1, the T-fitting connector can be used by the operator as a handle, and the handle can be moved relative to the proximal end of the outer catheter with sufficient force to overcome the friction between the collapsed guard and sealing structure and the interior wall of the respective catheter. As can be appreciated by those skilled in the art, the outer catheter may also be moved relative to the inner catheter for the same purpose. In the extended position, the guard and sealing structure is in the open configuration so that the infusion opening and the aspiration opening can transport fluid therethrough. Blood from the body vessel can then be aspirated through the aspiration opening, and transported to the extracorporeal treatment unit for treatment. Following treatment, treated blood can also be transported from the extracorporeal treatment unit, and infused into the body vessel through the infusion opening. In one application, transport of blood to a dialyzer and return of the treated fluid to the body vessel follows a path as known in the art, and need not be further discussed for an understanding of the present invention.

Drawings in the figures illustrating various embodiments are not necessarily to scale. Some drawings may have certain details magnified for emphasis, and any different numbers or proportions of parts should not be read as limiting, unless so designated in the present disclosure. Those skilled in the art will appreciate that embodiments not expressly illustrated herein may be practiced within the scope of the present invention(s) of this disclosure, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention(s) of this disclosure.

I claim:
1. A catheter assembly for use in the extracorporeal treatment of a body fluid, comprising:
   an outer tubular member having a passageway extending therethrough and a distal end opening;
   an inner tubular member having a lumen extending therethrough and a distal end opening together defining a first passage of fluid in a first direction, the inner tubular member situated within the passageway of the outer tubular member to define an annular lumen therebetween, the annular lumen and the distal end opening of the outer tubular member defining a second passage of fluid in a second direction, opposite the first direction; and
   a collapsible sealing structure comprising a flared portion having a wall made of a resilient material such that the flared portion is resiliently biased toward an open configuration, the flared portion coupled to the inner tubular member and axially movable between a first position and a second position, where, in the first position, the flared portion is axially extended from the outer tubular member to protect and facilitate fluid flow through the distal end openings of the respective inner and outer tubular members, and where, in the second position, the flared portion is collapsed to form a seal at both of the distal end openings of the respective inner and outer tubular members to inhibit fluid flow therethrough, the wall of the flared portion having a thickness such that the flared portion, when in the second position, seals the lumen by contact between portions of the flared portion.

2. The catheter assembly of claim 1, where the sealing structure comprises an enlarged portion configured to position at least one of the distal end opening of the inner tubular member and the distal end opening of the outer tubular member away from vessel contact.

3. The catheter assembly of claim 1, where the sealing structure is an enlarged distal tip configured to sealably engage at least one of the distal end opening the inner tubular member and the distal end opening of the outer tubular member.

4. The catheter assembly of claim 3, where the enlarged distal tip is configured to flare from a proximal tip to a distal base, and includes an access opening extending through the proximal tip and the distal base, where the proximal tip is coupled to the inner tubular member to extend the distal base distally, and the access opening is in communication with the first passage of fluid.

5. The catheter assembly of claim 4, where the sealing structure is radially movable from an open configuration to a collapsed configuration, where, in the open configuration, a portion of the enlarged distal tip is sized radially greater than the outer tubular member, and where, in the collapsed configuration, a substantial portion of the enlarged distal tip is configured to fit within the passageway of the outer tubular member.

6. The catheter assembly of claim 5, where, in the collapsed configuration, the flared portion of the enlarged distal tip is engaged with an interior wall of the outer tubular member to form said seal at the distal end opening of the outer tubular member, and an interior surface that defines the access opening of the enlarged distal tip is collapsed in on itself to form said seal at the distal end opening of the inner tubular member.

7. A catheter assembly for use in the extracorporeal treatment of a body fluid from a body vessel, comprising:
an outer tubular member and an inner tubular member situated within the outer tubular member to define an annular lumen, the inner tubular member having a lumen extending therethrough and a distal end opening to define a first fluid passage, the inner tubular member being connectable to an extracorporeal treatment unit to one of infuse or aspirate fluid in a first direction through the first fluid passage, the annular lumen and a distal end opening of the outer tubular member together defining a second fluid passage, the outer tubular member being connectable to the extracorporeal treatment unit to the other of infuse or aspirate fluid in a second direction, opposite the first direction, through the second fluid passage; and
a collapsible distal tip comprising a flared portion having a wall made of a resilient material such that the flared portion is resiliently biased toward an open configuration, the flared portion coupled to the inner tubular member, where, in a first position, the flared portion of the distal tip is radially extended beyond the outer tubular member to protect and facilitate fluid flow through the distal end openings of the respective inner and outer tubular members, and where, in a second position, the flared portion of the distal tip is at least partially collapsed to form a seal at both of the distal end openings of the respective inner and outer tubular members to inhibit fluid flow therethrough, the wall having a thickness such that the flared portion, when in the second position, seals the lumen by contact between portions of the flared portion.

8. The catheter assembly of claim 7, where the distal tip further comprises an outward extended portion configured to position at least one of the distal end opening of the inner tubular member and the distal end opening of the outer tubular member away from vessel contact when the distal tip is in the first position.

9. The catheter assembly of claim 7, where the flared portion of the distal tip comprises a hollow portion to facilitate radial collapsibility of the distal tip when moved to the second position.

10. The catheter assembly of claim 1, further comprising a proximal handle coupled to a proximal end of the outer tubular member, the proximal handle having a first bore and a second bore branching from the first bore and in communication with the first bore, the first bore receiving the inner catheter, the second bore in communication with the annular lumen, the proximal handle further comprising an actuation member coupled to a proximal end of the inner tubular member, and extendable from a proximal end of the handle, the actuation member configured to move the inner tubular member relative to the outer tubular member so that the flared portion is movable between the first and second positions.

11. The catheter assembly of claim 7, further comprising a proximal handle coupled to a proximal end of the outer tubular member, the proximal handle having a first bore and a second bore branching from the first bore and in communication with the first bore, the first bore receiving the inner catheter, the second bore in communication with the annular lumen, the proximal handle further comprising an actuation member coupled to a proximal end of the inner tubular member, and extendable from a proximal end of the handle, the actuation member configured to move the inner tubular member relative to the outer tubular member so that the flared portion is movable between the first and second positions.

12. The catheter assembly of claim 1, where the flared portion comprises an outer lip, the outer lip contacting a distal edge of the distal end opening of the outer tubular member in the second position.

13. The catheter assembly of claim 6, where the flared portion comprises an outer lip, the outer lip contacting a distal edge of the distal end opening of the outer tubular member in the collapsed configuration.

14. The catheter assembly of claim 7, where the flared portion comprises an outer lip, the outer lip contacting a distal edge of the distal end opening of the outer tubular member in the second position.

* * * * *